Figure 1:
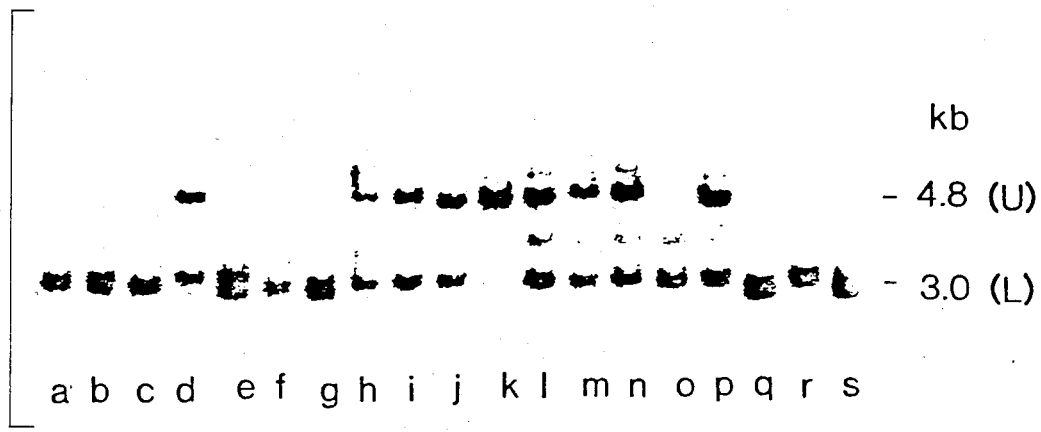

United States Patent [19]

Owerbach et al.

[11] Patent Number: 4,623,619

[45] Date of Patent: Nov. 18, 1986

[54] METHOD FOR THE DETERMINATION OF LIABILITY IN HUMAN INDIVIDUALS TO DEVELOP ATHEROSCLEROSIS

[75] Inventors: David Owerbach; Jørn Nerup, both of Gentofte, Denmark

[73] Assignee: Nordisk Insulinlaboratorium, Gentofte, Denmark

[21] Appl. No.: 467,843

[22] Filed: Feb. 18, 1983

[30] Foreign Application Priority Data

Mar. 3, 1982 [DK] Denmark ................ 920/82

[51] Int. Cl.$^4$ .............. C12Q 1/68; C12N 15/00
[52] U.S. Cl. ................................. 435/6; 435/172.3; 435/317; 436/503; 436/504; 436/63; 436/94; 436/811; 935/27; 935/77; 935/78
[58] Field of Search ............ 436/503, 504, 63, 94, 436/804, 811, 817; 435/6, 91, 172.3, 253, 317; 536/27, 28, 29; 935/27, 76–78

[56] References Cited

U.S. PATENT DOCUMENTS

| | | |
|---|---|---|
| 4,293,652 | 10/1981 | Cohen . |
| 4,351,901 | 9/1982 | Bahl ............................ 435/68 |
| 4,356,270 | 10/1982 | Itakura ........................ 435/68 |
| 4,358,535 | 11/1982 | Falkow et al. ................. 435/5 |
| 4,366,246 | 12/1982 | Riggs .......................... 435/68 |
| 4,411,944 | 10/1983 | Gilbert et al. ................ 435/71 |
| 4,419,446 | 12/1983 | Howley et al. ................ 435/68 |

OTHER PUBLICATIONS

Rotwein, P. S. et al, New Eng. J. Med., vol. 308(2), pp. 65–71 (1-13-83).
Rotwein, P. et al, Science, vol. 213, pp. 1117–1120 (9-1981).
Bell, G. I. et al, Proc. Natl. Acad. Sci., U.S.A., vol. 78, pp. 5759–5763 (9-1981).
Owerbach, D. et al, Diabetes, vol. 31, pp. 275–277 (3-1982).
Ullrich, A. et al, Science, vol. 209, pp. 612–615 (1980).
Ullrich, A. et al, Nucleic Acids Research, vol. 10, pp. 2226–2240 (1982).
Bell, G. I. et al, Nucleic Acids Research, vol. 8, pp. 4091–4108 (1980).
Owerbach, D. et al, Nature, vol. 286, pp. 82–84 (1980).
Bell, G. I. et al, Nature, vol. 284, pp. 26–32 (1980).
Owerbach, D. et al, Diabetes, vol. 30, pp. 267–270 (1981).
Owerbach, D. et al, The Lancet, vol. I, pp. 880–883 (1982).
Bell, G. I. et al, Nature, vol. 295, pp. 31–35 (1982).
Owerbach, D. et al, Diabetologia, vol. 21, p. 311, Abstract 387 (1981).
Harper, M. E. et al, Proc. Natl. Acad. Sci., U.S.A., vol. 78, pp. 4458–4460 (1981).
Owerbach, D. et al, The Lancet, vol. 2(8311), pp. 1291–1293 (12-1982).
Cochet, M. et al, Nature, vol. 297, pp. 335–339 (1982).
Grosschedl, R. et al, PNAS, U.S.A., vol. 79, pp. 297–301 (1982).
Corden, J. et al, Science, vol. 209, pp. 1406–1414 (1980).
DNA Sequence Flanking the Insulin Gene on Chromosome-11 Confer Risk of Atherosclerosis, Poulsen et al, Lancet, 2/4/84, p. 250.
Possible Association between DNA Sequences Flanking the Insulin Gene and Atheroschlerosis Owerbach, et al, Lancet, 12/11/82.
A Genetic Marker for Atherosclerosis, Manorup-Poulsen et al, Lancet, May 19, 1984.

Primary Examiner—Charles F. Warren
Assistant Examiner—M. Moskowitz
Attorney, Agent, or Firm—Ladas & Parry

[57] ABSTRACT

Liability in human individuals to develop non-insulin-dependent diabetes mellitus (NIDDM) and/or atherosclerosis is determined by restriction enzyme mapping of DNA from a human individual using a probe selected from the group consisting of (i) cDNA complementary to the mRNA coding for the human insulin,
(ii) human genomic DNA containing the actual insulin gene,
(iii) DNA sequences of human genomic DNA located within $20 \times 10^6$ base pairs from the insulin gene in either direction, and examining the distribution of DNA fragments for the appearance of insertion sequences of approximately 1600 to 2300 base pairs (U alleles) the occurrence of which indicates a liability for said individual to develop elevated blood glucose concentrations and/or atherosclerosis and in homozygous form a liability to develop NIDDM.

6 Claims, 3 Drawing Figures

METHOD FOR THE DETERMINATION OF LIABILITY IN HUMAN INDIVIDUALS TO DEVELOP ATHEROSCLEROSIS

The present invention concerns a method for the determination of liability in human individuals to develop atherosclerosis.

Diabetes mellitus (DM), a syndrome characterized by insufficient insulin secretion, hyperglycemia and propensity to develop universal microangiopathy, neuropathy and atherosclerosis, is a common condition affecting 1-2 percent of Caucasian populations. DM is common in all ethnic groups, its prevalence increases with age and more than 5 percent of individuals of more than 65 years of age have DM. Two major types of DM exist: Insulin-dependent diabetes mellitus (IDDM) (type 1 diabetes) comprises 10-15 percent of all DM and is characterized by a selective pancreatic beta-cell destruction, a very low, if any, insulin secretion, an absolute requirement for exogenous insulin, a low age of onset (although cases do occur in all ages) and a high prevalence of autoantibodies directed against antigenic determinants of the beta-cells. Recently IDDM was shown to be strongly associated with two alleles (HLA-DR3 and DR4) of the HLA-D/DR locus on chromosome 6. In non-insulin-dependent diabetes mellitus (NIDDM) (type 2 diabetes), representing 85-90 percent of all DM, insulin secretion is preserved, and such cases can be treated with dietary changes often combined with oral antidiabetic drugs. NIDDM is probably a rather heterogenous condition, but age of onset is relatively late in life.

Studies of identical twins have shown the hereditary component in NIDDM to be stronger than in IDDM, but no genetic markers have been proven to be associated with the occurrence of NIDDM.

One possible cause for NIDDM is the presence of an abnormal insulin molecule. Structurally abnormal insulins have been found in two families with hyperproinsulinaemia and an abnormal insulin in one individual with diabetes mellitus, but their occurrence appears to be rare. Alternatively, regulatory sequences linked to the insulin gene could occur in NIDDM individuals thus causing the glucose intolerance or hyperglycemia.

A polymorphic region of DNA on the short arm of chromosome 11 beginning 363 basepairs (bp) before the transcriptional start point of the human insulin gene has been partially characterized; See G. I. Bell et al., Proc. Natl. Acad. Sci. USA, Vol 78, No. 9, pp.5759-5763, September 1981 and G. I. Bell et al., Nature Vol 295, Jan. 7, 1982. The polymorphic region can be detected using a number of different restriction endo-nucleases and results from insertions and deletions of DNA, part or all of which are related to a family of tandemly repeated nucleotides whose structure is related to ACAGGGGTGTGGG. The insertions in this region are primarily of two size classes: 0-600 bp and 1600-2200 bp; restriction fragments possessing insertions of 600-1600 bp are rarely observed. The role of the insertion sequences with respect to glucose regulation and development of diabetes is unknown.

P. Rotwein et al., Science, Vol. 213, pp. 1117-1120, Sept. 4, 1981, have investigated polymorphism in the 5'-flanking region of the human insulin gene and its possible relation to type 2 diabetes. Their data, however, do not show a simple relation between the presence of large insertions and disease. There is no indication in this paper that the large insertions can be used as genetic markers of NIDDM.

An extremely common form of atherosclerosis is a syndrome characterized by deposits containing cholesterol and lipid material in medium and large size arteries. Clinical manifestations of this type of atherosclerosis, called macroangiopathy, result in myocardial infarctions, strokes and peripheral vascular disease. High frequencies of macroangiopathy are already evident in individuals in their fourties and it is estimated that more than 90% of individuals over 50 years of age have detectable atherosclerosis. Macroangiopathy is by far the most common course of death in the general population.

Macroangiopathy is increased in certain diseases, in particular non-insulin-dependent diabetes mellitus. Obesity has also been found to be related to increased levels of arterial blood pressure and an increased incidence of cardiovascular disease. However, no genetic markers exist for atherosclerosis.

An object of the present invention is to provide a method for the determination of liability in human individuals to develop atherosclerosis by detecting disease susceptibility sequences or sequences linked thereto in human DNA.

Figure 2:
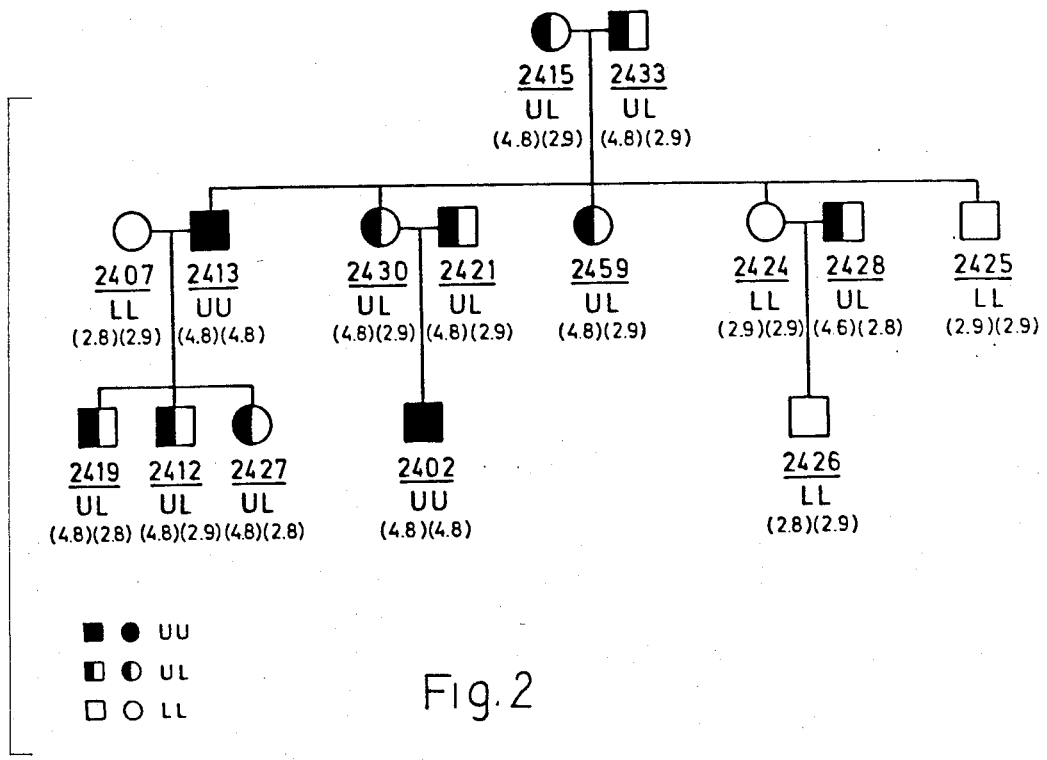
Figure 3:
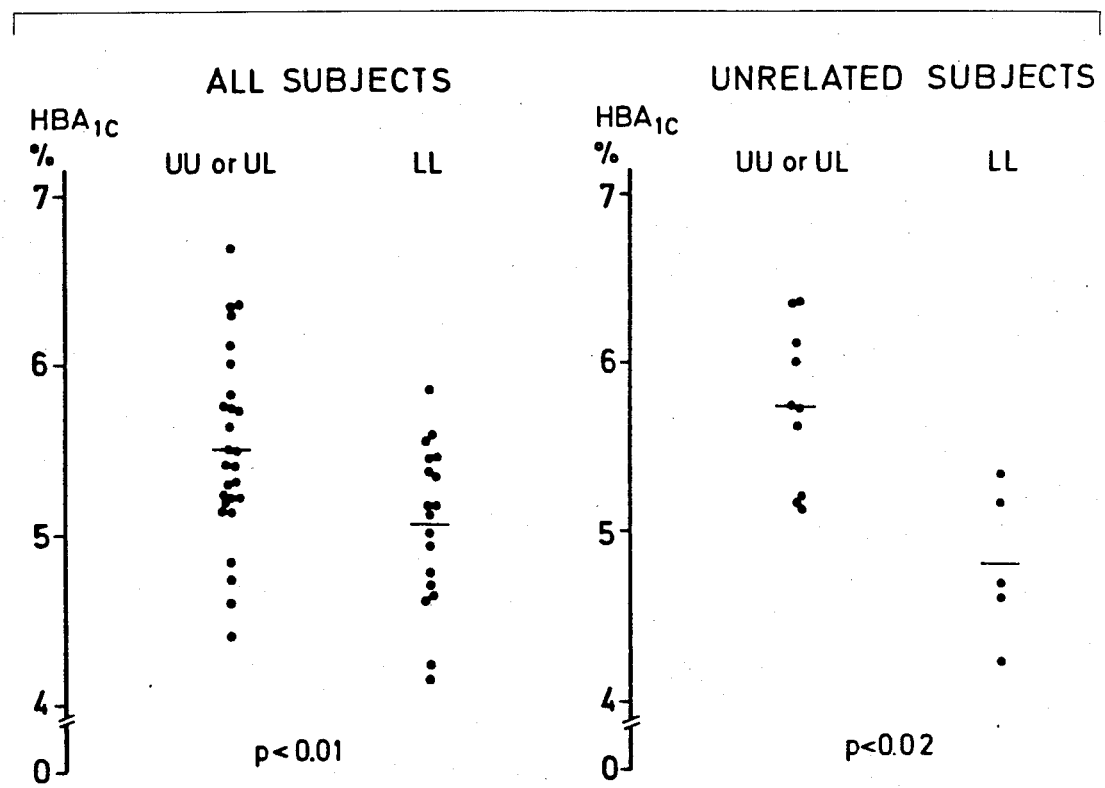

FIG. 1 is an autoradiogram of BGL I insulin-related DNA sequences from 19 individuals (A through S) obtained by probing BGL I restricted DNA with a 32 P-labelled insulin Ø-DNA, FIG. 2 is a small segment of a family tree showing their U and L genotypes, and FIG. 3 is a comparison of haemoglobin A-1C levels in the groups containing U alleles and being homozygous LL, respectively, of a large family and in the corresponding groups of the subset of unrelated subjects married into the family.

The method of the invention is based on the detection of specific size classes of DNA sequences located near the human insulin gene on the short arm of chromosome 11 and comprises the following steps:

(a) providing a probe selected from the group consisting of
  (i) cDNA complementary to the mRNA coding for the human insulin,
  (ii) human genomic DNA containing the actual insulin gene,
  (iii) DNA sequences of human genomic DNA located within $20 \times 10^6$ base pairs from the insulin gene in either direction;
(b) using said probe for restriction enzyme mapping of DNA from a human individual;
(c) examining the distribution of DNA fragments for the appearance of insertion sequences of approximately 1600 to 2200 base pairs (U allele);
(d) the occurrence of said U allele indicating a liability for said individual to develop atherosclerosis.

Utilizing standard Recombinant DNA technology it has been possible to isolate and clone a human insulin gene and its flanking sequences. This clone isolated by the inventor, David Owerbach, from his own tissue, has been designated λHI-DO. The 5'-flanking sequences of the clone include a large insertion sequence of approximately 1600 bp. The clone λHI-DO may be used as a probe in the method according to the invention.

Purified genomic DNA fragments containing insulin gene sequences are radioactively labelled. The labelled cDNA preparations are used to probe human DNA by the Southern hybridization technique. In short, DNA, isolated from peripheral blood lymphocytes, are treated with restriction enzymes to yield DNA-fragments of variable sizes. The DNA-fragments are separated into fragments of different molecular mass by gel electrophoresis and transferred to filters which bind the DNA. After exposure to the labelled genomic DNA probe, which only will bind to (hybridize) DNA-fragments containing related nucleotide sequences, binding of radioactive probe to DNA-fragments of different sizes is identified by autoradiography. For the technique used, see *Genetic Engineering* 1, ed. Robert Williamson, Academic Press 1981, pp. 72–81.

DNA sequences of two size classes are detected by this method: one class showing insertion sizes within the previously mentioned range of 1600–2200 bp, which we have designated the U allele (upper electrophoretic type), and the other class showing insertion sizes within the previously mentioned range of 0–600 bp, which have designated the L allele (lower electrophoretic type) (example 1). These sequences are shown to be real alleles that segregate as classical genetic markers (example 2). The U alleles are associated with elevated mean blood glucose concentrations (example 3). The homozygous presence of the U allele (UU genotype) is associated with NIDDM and can therefore be used for assessing risk for developing NIDDM (example 4). Further, the presence of the UU or UL genotype can be used to evaluate risk for NIDDM as well as non-diabetic individuals to develop disorders associated with atherosclerosis (example 5).

EXAMPLE 1

A $^{32}$P-labelled insulin cDNA was used to study restriction enzyme length polymorphism in DNA isolated from a total of 19 individuals.

The human DNA was digested with Bgl I and resulting fragments separated by slab gel electrophoresis and subjected to the Southern hybridization technique. An autoradiogram of Bgl I insulin-related DNA sequences is shown in FIG. 1.

Channels a–s are the hybridization patterns obtained from 19 non-related individuals. λDNA digested with Hind III (Bethesda Research Laboratories) was used as molecular weight markers. Hybridization was seen at approximately 3.0 kb (L allele) and 4.8 kb (U allele). Within each size class there was variation: 2.8–3.0 kb and 4.6–5.0 kb in these 19 individuals. Individuals a, c, f, o, r, s were homozygous for the L allele, d, h, i, j, l, m, n and p heterozygous UL and individual k homozygous UU. Individuals b, e, g and q (LL) had two distinguishable L alleles. In addition to the major hybridization sequences of approximately 3.0 and 4.8 kb, two minor sequences at approximately 3.7 and 5.5 kb were also detected. These minor sequences are due to partial digestions.

EXAMPLE 2

The presence of U and L alleles were investigated in 53 members of a large family and found to exist in four sizes: 4.8 kilobases (kb), 4.6 kb, 2.9 kb and 2.8 kb. The distribution of the sequences is comparable with the classical Mendelian segregation, a small segment of the family amd their insulin genotypes are shown in FIG. 2.

EXAMPLE 3

Haemoglobin $A_{1c}$-levels (HbA$_{1c}$) are strongly correlated with mean blood glucose concentrations over a period of weeks (P. Aa. Svendsen et al., Diabetologia, 21, p. 332 (1981)). 53 individuals of a large family (see example 2) were grouped into those containing U alleles and those being homozygous LL and HbA$_{1c}$ levels were compared both in all subjects and the subset of unrelated subjects married into the family. The results are indicated in FIG. 3. Stable HbA$_{1c}$ was higher in UU+UL individuals than in LL individuals (FIG. 3). UU+UL individuals differed from LL individuals also among the unrelated individuals. Mean values for all subjects investigated were for UU+UL: 5.50% and for LL-individuals 5.06% (p<0.01). For unrelated individuals the values were 5.74% and 4.81%, respectively (p<0.02). The UU+UL individuals ranged in age from 10–74 and the LL individuals from 10–81. Mean ages, 37.3 (UU+UL) and 34.3 (LL), were not statistically different. These results indicate that the U allele is associated with elevated blood glucose concentrations.

EXAMPLE 4

47 NIDDM patients were randomly selected from those consecutively attending the outpatient clinic of Steno Memorial Hospital, Gentofte, Denmark. Clinical details are shown in table I. All had been treated by diet only or by diet plus sulphonylureas since diagnosis. Only 1 obese patient required insulin for correction of hyperglycaemia after several years of oral treatment with hypoglycaemic drugs.

From the Glostrup population study we selected groups of control subjects born in 1914.

IGT GROUP 45 subjects who had met the W.H.O. criteria of impaired glucose tolerance (IGT) when tested at 50 and 60 years of age were retested by oral glucose tolerance tests (OGTT) for this study. 14 had normal glucose tolerance, 4 had become diabetic, and 27 still had IGT and were chosen as the IGT group.

NORMAL GROUPS I AND II 52 subjects with fasting blood glucose concentrations <75 mg/dl (4.2 mmol/l) at 50 years of age and with normal OGTTs at 60 were divided into two groups. Normal group I consisted of 29 subjects who now had fasting blood glucose concentrations ≦5.0 mmol/l and stable HbA$_{1c}$ values <6.4%. Normal group II contained 23 subjects who at the time of this study had fasting blood glucose concentrations of 5.1–7.0 mmol/l.

All subjects were investigated for U and L alleles as previously described. The two-tailed Fisher's exact test was used for statistical analysis. 5% was chosen as the level of significance.

The genotype frequencies of UU, UL and LL in the NIDDM patients are reported in table I, and those in the IGT and the two normal groups are shown in table II.

TABLE I

Frequencies of UU, UL and LL genotypes in the NIDDM patients

| Genotype | No. | Mean age ± SD (yr) | | Mean duration NIDDM ± SD |
|---|---|---|---|---|
| | | Current | At diagnosis | |
| UU | 8 | 62 ± 7 | 55 ± 7 | 8.2 ± 8.9 |
| UL | 17 | 64 ± 6 | 56 ± 8 | 8.1 ± 6.4 |
| LL | 22 | 63 ± 10 | 56 ± 10 | 7.2 ± 6.9 |

TABLE II

Frequencies of UU, UL and LL genotypes in the non-diabetic groups

| Group | Mean age + SD (yr) | No. with genotype UU | UL | LL |
|---|---|---|---|---|
| IGT (n = 27) | 67 ± 1 | 1 | 13 | 13 |
| Normal I (n = 29) | 67 ± 1 | 0 | 16 | 13 |
| Normal II (n = 23) | 67 ± 1 | 2 | 8 | 13 |

Comparing the frequency of UU and UL + LL between:
normal I and NIDDM, p = 0.333;
normal I + II and NIDDM, p = 0.0535; and
normal I + II + IGT and NIDDM, p = 0.0244.

The homozygous UU genotype was quite common in the NIDDM group (17%) but rare in the IGT and normal groups. The difference in the UU frequency between NIDDM and normal group I was significant (p=0.0333), but the difference in frequency between the NIDDM group and the IGT group and normal group II were not significant. However, the UU frequency in all the non-diabetic control groups together (normal I+II+IGT) was significantly less than that in the NIDDM group (p=0.0244).

EXAMPLE 5

All the subjects in the IGT and the two normal groups from the previous example were asked to answer a questionnaire on cardiovascular disease, supplemented with questions about symptoms and signs of cerebrovascular large-vessel disease. Previously diagnosed myocardial infarctions, classical symptoms of angina pectoris or intermittent claudication, and the occurrence of paralyses thought to be due to apoplexia cerebri were noted. Subjects reporting one or more of these disorders were classified as having macroangiopathy. Similarly, symptoms and signs of macroangiopathy were noted from the records of the NIDDM patients. The two-tailed Fisher's exact test was used for statistical analysis. 5% was chosen as the level of significance.

TABLE III

Clinical details of NIDDM patients

| Genotype | No. | Mean age ± SD (yr) Current | At diagnosis | Mean duration NIDDM ± SD | No. with macro-angiopathy (%) |
|---|---|---|---|---|---|
| UU | 8 | 62 ± 7 | 55 ± 7 | 8.2 ± 8.9 | 6(75*) |
| UL | 17 | 64 ± 6 | 56 ± 8 | 8.1 ± 6.4 | 7(41) |
| LL | 22 | 63 ± 10 | 56 ± 10 | 7.2 ± 6.9 | 6(27*) |

*UU vs LL: p = 0.0483.

In the NIDDM group the prevalence of macroangiopathy was significantly higher in the UU than in the LL subjects (table I; p=0.0483). Macroangiopathy assessed by questionnaire was less frequent in the IGT group (29%) and in the normal groups (normal I 27% and normal II 33%) than in the NIDDM group (40%), but these differences were not significant.

5 Controls (3 in normal I and 2 in normal II) did not answer the questionnaire. The U/L genotypes of these subjects were UL (2) and LL (3). The IGT group and the remaining subjects in the two normal groups showed the prevalence of macroangiopathy reported in table IV.

TABLE IV

Prevalence of macroangiopathy in relation to UU, UL and LL genotypes in the non-diabetic groups

| | Age | Number with macroangiopathy/ total number of individuals | |
|---|---|---|---|
| | | UU and UL | LL |
| Impaired glucose tolerance (n = 27) | 67 ± 1 | 6/14 | 2/13 |
| Normals I (n = 26) | 67 ± 1 | 6/14 | 1/12 |
| Normals II (n = 21) | 67 ± 1 | 6/10 | 1/11 |
| Total (n = 74) | | 18/38 (47 percent) | 4/36 (11 per cent) |

Statistics (Fisher's exact test):
Normals I + II + IGT: UU and UL vs LL p = 0.001
p = 0.0040

Normals I + II: UU and UL vs LL

In all three non-diabetic groups macroangiopathy was more frequent in UU and UL subjects than in LL homozygous subjects. When these three groups were analysed together, macroangiopathy was significantly more common in UU and UL subjects than in LL homozygous subjects (47% vs 11%; p=0.0011). In the two normal control groups macroangiopathy was again significantly more frequent in UU and UL then in LL subjects (p=0.0040).

Our results indicate that the U alleles, in the polymorphic region flanking the insulin gene on chromosome 11, influence the development of macroangiopathy in NIDDM patients as well as in non-diabetic controls.

We claim:
1. A method for the determination of liability in human individuals to develop atherosclerosis which comprises the following steps:
    (a) providing a probe selected from the group consisting of
        (i) cDNA complementary to the mRNA coding for the human insulin,
        (ii) human genomic DNA containing the actual insulin gene,
        (iii) DNA sequences of human genomic DNA located within $20 \times 10^6$ base pairs of the insulin gene in either direction;
    (b) using said probe for restriction enzyme mapping of DNA from a human individual;
    (c) examining the distribution of DNA fragments for the appearance of insertion sequences of approximately 1600 to 2200 base pairs (U alleles);
    (d) the occurrence of said u allele indicating a liability for said individual to develop atherosclerosis.

2. A method according to claim 1 in which the probe is human genomic DNA containing the insulin gene or DNA sequences up to 4000 base pairs upstream of the 5'-end of the insulin gene.

3. A method according to claim 1 in which the probe consists of DNA sequences derived from the Bgl I fragment of human genomic DNA which contains the insulin gene.

4. A method according to claim 3 in which the probe consists of DNA sequences from the Bgl I fragment in the region of from 0 to 4000 base pairs upstream of the 5'-end of the insulin gene.

5. A method according to claim 1 in which human DNA is treated with one or more restriction enzymes and the resulting fragments separated into fragments of different molecular mass by gel electrophoresis and transferred to a filter covalently binding the DNA, whereafter the filter is exposed to the radioactively labelled probe and binding of the probe to DNA fragments of specific sizes is identified by autoradiography.

6. A method according to claim 5 in which the restriction enzyme is Bgl I and the probe is a $^{32}$P-labelled genomic DNA fragment containing insulin gene sequences, and that the fragment distribution is examined for the appearance of a fragment of approximately 4.8 kb.

* * * * *